United States Patent [19]

Cierpka

[11] Patent Number: 4,740,506
[45] Date of Patent: * Apr. 26, 1988

[54] BIS(TRIMETHAPHAN)-NITROPRUSSIDE SALTS AND USE THEREOF FOR BLOOD PRESSURE REDUCTION

[76] Inventor: Henning Cierpka, 1A Stockackerstrasse, Reinach, Switzerland

[*] Notice: The portion of the term of this patent subsequent to Jan. 26, 2005 has been disclaimed.

[21] Appl. No.: 456,128

[22] Filed: Jan. 6, 1983

[30] Foreign Application Priority Data

Feb. 22, 1982 [CH] Switzerland ............................ 388/82
Feb. 22, 1982 [CH] Switzerland ............................ 389/82

[51] Int. Cl.[4] ..................... A61K 31/38; C07D 495/16
[52] U.S. Cl. ..................................... 514/185; 548/107
[58] Field of Search ................. 548/107; 429/245; 514/185

[56] References Cited
PUBLICATIONS

MacRae et al., "Anaestheria", 36, pp. 312–315, (1981).

*Primary Examiner*—Glennon H. Hollrah
*Assistant Examiner*—D. B. Springer
*Attorney, Agent, or Firm*—Sandler & Greenblum

[57] ABSTRACT

There are described the novel compound bis-(trimethaphan)-nitroprusside of formula

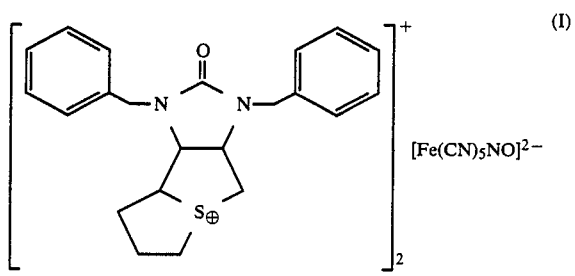

and solvates, especially hydrates or alcoholates thereof, as well as a process for the manufacture thereof from an alkali nitroprusside and a soluble trimethaphan salt, especially sodium nitroprusside and trimethaphan camsylate, in solution, especially in water.

Furthermore, there are described pharmaceutical compositions which contain the novel active substance (I) in solid form, in form of concentrated solutions or in form of diluted solutions suitable for infusion purposes.

In particular there are described compositions which contain (I) in concentrated solution in at least 40% ethanol or in solid form as well as compositions which contain, in addition to (I), a soluble, physiologically acceptable thiosulphate, in particular sodium thiosulphate.

The preparation of infusion solutions from the concentrated solutions or mixtures, the preparation of an especially well soluble micronized mixture of (I) and thiosulphate and the use of the concentrate for the preparation of infusion solutions are also described.

The compound (I) and its solvates and the pharmaceutical compositions containing (I) are suitable for therapeutic use, particularly in the lowering of blood pressure, in the achievement of peripheral vasodilation, in the elimination of arterial spasms and/or in the reduction of myocardial oxygen consumption and of the work load of the heart after heart attack.

25 Claims, 3 Drawing Sheets

FIG. 1.

FIG. 3.

BIS(TRIMETHAPHAN)-NITROPRUSSIDE SALTS AND USE THEREOF FOR BLOOD PRESSURE REDUCTION

BACKGROUND OF THE INVENTION

Sodium nitroprusside is a known infusion preparation for the rapid and controlled lowering of the blood pressure in the case of operations or hypertension crises and for reducing the work load of the heart, e.g. in the case of heart attack. However, it has disadvantages which restrict the use of this valuable and extraordinarily well controllable medicament. Thus, it decomposes in the body very rapidly with the formation of 5 moles of cyanide per molecule. Since cyanide is an acutely toxic agent which blocks the respiratory chain and paralyses the respiratory centre, SNP must be used in order to avoid an accumulation of toxic cyanide concentrations in the blood serum only with the strictest maintenance of prescribed highest dosages and even then only for a short time.

In common with other vasodilators SNP has the disadvantage that the desired rapid and powerful lowering of blood pressure leads very frequently to an activation of the so-called counter-regulation, whereby, in turn, the amount of circulating hormones which increase blood pressure (adrenalin, noradrenalin and angiotensin II) and of renin is greatly increased. This causes, especially in young patients, a strong tendency to increased blood pressure which can be compensated only by successive increase of the dosage of SNP to be infused (tachyphylaxis). If in such cases the administration of SNP is not discontinued, a dangerous increase of the cyanide level in the blood serum can arise very rapidly, even on short-term use of SNP, because of the over-dosage which then occurs. If in this case the tolerance limit of about 0.8 $\mu$g of CN/100 ml of blood plasma is exceeded, severe cyanide poisoning and even death can arise (see Anesthesiology 47, 441–448 (1977); Bull. Med. Legale Toxicol. 21, 215–224 (1978); Amer. J. Obstet. Gynecol. 139, 708–711 (1981)).

A further disadvantage of SNP is the appearance of the so-called "rebound" hypertension owing to persistent counter-regulation after termination of the SNP infusion. (New England J Med. 302, 1029–1030 (1980); Anesthesiology 44, 345–348 (1976)). Since this "rebound" hypertension occasionally causes blood pressure levels which lie far above the initial blood pressure, secondary bleedings can occur in newly operated patients and dangerous blood perfusion disorders in the brain owing to oedema formation can occur in predisposed patients.

Since, on the other hand, SNP is at present the most active agent for the controlled lowering of blood pressure, e.g. during operations, attempts have been made to eliminate the mentioned disadvantages.

MacRae has recently proposed (Anaesthesia 36,312–315 (1981)) to infuse SNP together with the ganglionic blocking agent trimethaphan camsylate (TMC). in the weight ratio 1:10. He reported that thereby the amount of SNP required for the same lowering of the blood pressure was considerably lower.

TMC and its blood pressure-lowering activity are known and TMC is therefore employed therapeutically (in spite of its lower activity) similarly to SNP, i.e. as an infusion preparation for the controlled short-term lowering of blood pressure. However, TMC displays, in turn, a series of side effects which restrict its use.

Thus, in addition to such side effects as tachycardia, mydriasis, cycloplegia, urine retention, xerostomia and constipation, which occur by blockade of the parasympathetic ganglia, nausea or vomiting can arise in sensitive patients and, especially in children and aged patients, allergies can arise owing to histamine liberation.

Moreover, trimethaphan camsylate must not be used alone in the case of operations in the region of the gastro-intestinal tract.

The dosage of SNP required for the controlled lowering of blood pressure is on average about 3 $\mu$g/kg body weight per minute, that of TMC about 30 $\mu$g/kg per minute. Corresponding to this ratio of the pharmacological activities the concentrations of the infusion solutions usually used are thus 0.01 and 0.1%, respectively. The ratio of 1:10 proposed by MacRae (loc. cit.) therefore corresponds to the relative strengths of the two agents.

According to MacRae, the clinical activities of the single components in the 1:10 infusion mixture appear to be additive or even become potentiated, while the corresponding side-effects (because of their qualitative difference) are relatively diminished. Thus, seeing that ad hoc preparation of the mixture in the clinic is complicated and, because of the errors which are possible in practice, even dangerous, it appeared advantageous to develop an appropriate combination product.

However, an obstacle to the development of such a combination product was the fact that the two single drugs are not compatible in concentrated form. When preparing the mixture either drug had firstly to be diluted to infusion strength, and these solutions could then be mixed shortly before the infusion. Because of the limited storage stability of dilute solutions of TMC and SNP and because of the known extreme light sensitivity of SNP solutions, such a highly diluted combination product is, in any event, not suitable as a commercial product.

The observation that the adduct of the two active ions, the hitherto unknown bis-(trimethaphan)-nitroprusside (I), can be isolated in pure form and in high yield and can be processed to a storable pharmaceutical composition was therefore surprising.

BRIEF DESCRIPTION OF THE INVENTION

In accordance with the present invention there is provided the complex salt bis-(trimethaphan)-nitroprusside of formula This compound is novel and posseses interesting pharmacodynamic properties.

The invention relates to bis-(trimethaphan)-nitroprusside of formula I above, particularly (+)-bis-(trimethaphan)-nitroprusside, as well as solvates, particularly hydrates and alcoholates, thereof, the manufacture of these compounds, pharmaceutical compositions containing such a compound and the manufacture of such compositions as well as the use of such compounds and of such pharmaceutical compositions in the controlled lowering of blood pressure, in the achievement of peripheral vasodilation, in the elimination of arterial spasms and/or in the reduction of myocardial oxygen consumption and of the work load of the heart after heart attack.

DETAILED DESCRIPTION OF THE INVENTION

The compound of formula I, above, has the advantage that it is free from pharmacologically inactive material (sodium and camsylate ions), so that it has a considerably higher content of active material per weight unit: 1000 mg of the compound (I) in accordance with the invention contain the same amount of active material as 1575 mg of a mixture of 2 moles of TMC and 1 mole of SNP. Such a reduction of the content of pharmaceutically inactive material can improve the tolerance of infusion preparations quite considerably.

Furthermore, the surprising and unforeseeable pharmacological finding was made that not the mixture of equipotent amounts by weight (1:10) used by MacRae, but rather the molar ratio (1:2) present in the compound of formula (I) gives the maximum synergistic activity. This is evident, for example, from the following experiment:

The various infusion solutions listed below were infused i.v. in succession, with appropriate recovery intervals, into a male, spontaneously respiring cat weighing 3.7 kg under Nembutal narcosis, and the dosages required to achieve a given lowering of the blood pressure were determined.

Substances and mixtures of substances tested

A (+)-Bis-(trimethaphan)-nitroprusside
B SNP (commercial product NIPRIDE)
C TMC (commercial product ARFONAD)
D The combination of SNP and TMC (weight ratio 1:10 in accordance with MacRae)
E The combination of SNP and TMC (weight ratio 1:4).

For the preparation of the infusion solutions, the substances or their concentrated stock solutions were diluted with 0.9% sodium chloride solution to a uniform infusion strength of 9 mg/100 ml (90 $\mu$g/ml). All solutions were freshly prepared and infused with the exclusion of light (aluminium foil) corresponding to the dosages given below.

The values given in Table I hereinafter were determined graphically.

TABLE I

Infusion dosages ($\mu$g/kg · min) of the compounds A to E required to achieve a given lowering of the blood pressure

| Lowering of blood pressure (in mm Hg) | Infusion dosage required for this effect (in $\mu$g/kg · min) | | | | |
|---|---|---|---|---|---|
| | A | B | C | D | E |
| −20 | 1.5 | 1.7 | 6.0 | 4.3 | 2.9 |
| −30 | 2.3 | 3.6 | 18 | 10 | 5.1 |
| −40 | 3.5 | 7.0 | 55 | 29 | 8.6 |
| −50 | 5.8 | 23 | * | 110 | 11.4 |
| −55 | 7.8 | 75 | * | * | 27 |
| −75 | 40 | * | * | * | * |

* = Limit of activity and/or predominance of toxic side effects

From Table I the following conclusions can be drawn:

In the case of slight lowering of the blood pressure (to −30 mm Hg) A, B and E still have approximately comparable strengths of activity, although even in this range A surprisingly shows up best. In the case of greater lowerings of the blood pressure (and at the same time greater increases of the counter-regulation) not only B but also E distinctly fall off increasingly.

At about −55 mm Hg not only B but also E have reached the limit of their activity, i.e. with further increase in dosage only their toxic action increases.

C (TMC) is, as expected, significantly less active and reaches its limit of activity already at −40 mm Hg. D, the mixture of SNP and TMC (1:10) recommended by MacRae (loc. cit.), was also distinctly less active than SNP (B) alone. The limit of activity was in the case of D −50 mm Hg, however D was distinctly more active than C (TMC alone).

It was also surprising that A has a significantly higher limit of activity than all the other substances or mixtures.

In accordance with the present invention, bis-(trimethaphan)-nitroprusside and solvates thereof can be prepared by reacting a solution of an alkali nitroprusside with a soluble trimethaphan salt, separating the poorly soluble product from the more readily soluble accompanying salts and isolating said product.

The reaction is conveniently carried out in a solvent containing the desired solvating agent, particularly in aqueous solution or in a solution which contains water and/or alcohol. In a preferred embodiment of the process of the invention, sodium nitroprusside and trimethaphan camphorsulphonate are brought together in aqueous solution.

The present invention is also concerned with pharmaceutical compositions which contain the novel active substance bis-(trimethaphan)-nitroprusside (I) in concentrated form or in dilute form suitable for infusion purposes, processes for their manufacture as well as their therapeutic use.

In a preferred embodiment of its composition aspect, the invention is concerned with a concentrated stock solution of I in at least 40% ethanol, which can also be prepared in situ from an appropriate amount of I (contained, for example, in a vial or a dry ampoule) and a small amount of at least 40% ethanol (contained, for example, in a sterile ampoule), whereby the ethanol is preferably 50 to 95, especially about 60%. The amount of solvent for the preparation of the stock solution preferably amounts to at most 20 ml, especially 2–5 ml.

A dilute (about 0.01%) infusion solution can prepared from the concentrated stock solution at the place of use with a sterile conventional infusion liquid, such as 0.9% sodium chloride solution of 5% glucose solution. The dilute infusion solution of the active substance I are also part of the invention.

A further preferred embodiment of the composition aspect of the invention is concerned with mixtures of I with a physiologically acceptable thiosulphate which is soluble in water or aqueous ethanol, preferably an alkali thiosulphate, especially sodium thiosulphate or its pentahydrate. Also these mixtures can be present either already in concentrated solution in at least 40% ethanol (e.g. in a solvent ampoule) or as a solid mixture, preferably pulverized as finely as possible or micronized. In the latter case, the composition can be furnished together with a solvent ampoule containing the amount of solvent required for the preparation of the concentrated stock solution, but it is also suitable for the direct dissolution in the infusion liquid.

As the preferred solvent for the preparation of concentrated solutions of the mixture there is suitable at least 40%, preferably 45–60%, especially 50 to 55%, ethanol.

The mixture of I and thiosulphate should be present preferably at least in the weight ratio 1:1 and preferably at most in the weight ratio 1:40 (in the case of solid mixtures) or 1:20 (in the case of concentrated ampoule solutions).

The pharmaceutical infusion solutions obtained from the above concentrates or solid mixtures according to the processes described below serve, for example, for the rapid and controlled lowering of blood pressure, for the peripheral vasodilation, for the elimination of arterial spasms and for the reduction of the myocardial oxygen consumption and of the work load of the heart after heart attack.

The compound I contains the nitroprusside anion which is also present in sodium nitroprusside.

In the case of the therapeutic administration of the novel compound I the danger of cyanide poisoning is considerably lower, since I contains a lower amount by weight of cyanide (13.7%) than SNP 43.6%) and, moreover, it can be administered at lower dosages than SNP. However, the latent danger of an accumulation of dangerous amounts of cyanide in the plasma still exists in particular circumstances (e.g. in patients with greatly reduced endogenous thiosulphate level or owing to exhaustion of the endogenous thiosulphate reserves in the case of long term application, high dosages or in the case of erroneous over-dosage). It is also known that higher plasma concentrations of cyanide ($>10^{-5}$ µg/ml) can greatly impair the vasodilatory activity of SNP (Amer. J. Physiol. 237, H 185 - H 90 (1979)). Therefore, high cyanide concentrations in the plasma are considered as being a factor responsible for the occurrence of tachyphylaxis during the therapeutic administration of SNP (Anesthesiology 51, 563–564 (1979)).

It is also known that the toxicity of SNP can be reduced e.g. in mice and rabbits by simultaneous infusion of sodium thiosulphate (J. Pill, P. Engeser, M. Höbel, V. A. W. Kreye, Toxicology Letters, Suppl. 1, 156, p. 61 (1981)). These authors also proposed to use SNP and sodium thiosulphate in stoichiometric amounts (1:5 mol), i.e. to employ these agents in the weight ratio 1:4.16, whereby SNP is employed as the dihydrate (m.w. 298) and sodium thiosulphate is employed as the pentahydrate (m.w. 248.1).

The use of thiosulphate as a cyanide antidote has been known for a long time and is based on the fact that thiosulphate is the substrate of the enzyme rhodanase which converts cyanide into the not very toxic thiocyanate.

It therefore appears advantageous also to administer the compound I together with an amount of a water-soluble thiosulphate equivalent to the biologically liberated amount of cyanide.

In order to facilitate the control of the correct dosage for the physician, there comes into consideration for this purpose only a uniform pharmaceutical composition (mixture) of I and thiosulphate, which, if desired, is already dissolved or can be brought into solution in a simple manner.

Suitable thiosulphates are in principle all physiologically acceptable thiosulphates which are soluble in water and in aqueous ethanol, such as alkali thiosulphates, e.g. potassium thiosulphate or sodium thiosulphate ot its pentahydrate. However, sodium thiosulphate has to be given preference on practical reasons, because it is pharmacologically and clinically tested, has a very low toxicity ($LD_{50}$ in rats, i.v., 2500 mg/kg) and is furthermore readily obtainable.

Corresponding to the amount of nitroprusside anion there can formed from one mol of I (m.w.=947) 5 mol of cyanide, for the detoxification of which 5 mol of thiosulphate suffice in theory. The stoichiometric ratio (by weight) of I and sodium thiosulphate pentahydrate is thus 1:1.31 and the weight of sodium thiosulphate pentahydrate equivalent to the cyanide from 50 mg of I amounts to only 65.5 mg. This amount is thus significantly lower than the amount of sodium thiosulphate pentahydrate (208 mg) theoretically required for 50 mg of SNP.

Sodium thiosulphate is, however, used as a cyanide antidote (i.e. in the treatment of acute cyanide poisoning) in considerable excess, e.g. in dosages of 1 g up to 12.5 g, which have to be injected in aqueous solution and very slowly.

This excess is necessary in urgent cases of acute cyanide poisoning, since thiosulphate passes through biological membranes only very slowly and yet must be available rapidly and in large amount. However, the dosage can be reduced quite considerably in the case of prophylactic use. On the other hand, a certain excess is necessary, since thiosulphate is excreted relatively rapidly via the kidneys. It is therefore recommendable to use a multiple of the calculated stoichiometric thiosulphate dosage, e.g. up to 2000 mg per 50 mg of I (weight ratio 1:40).

For reasons of storage stability, medicaments intended for infusion are frequently marketed not as solutions, but in solid form. For obtaining an unobjectionable solution it is usual in such cases to prepare by means of a supplied solvent ampoule immediately prior to use a small amount of a concentrated solution and to dilute this to the infusion strength immediately.

Figure 1:
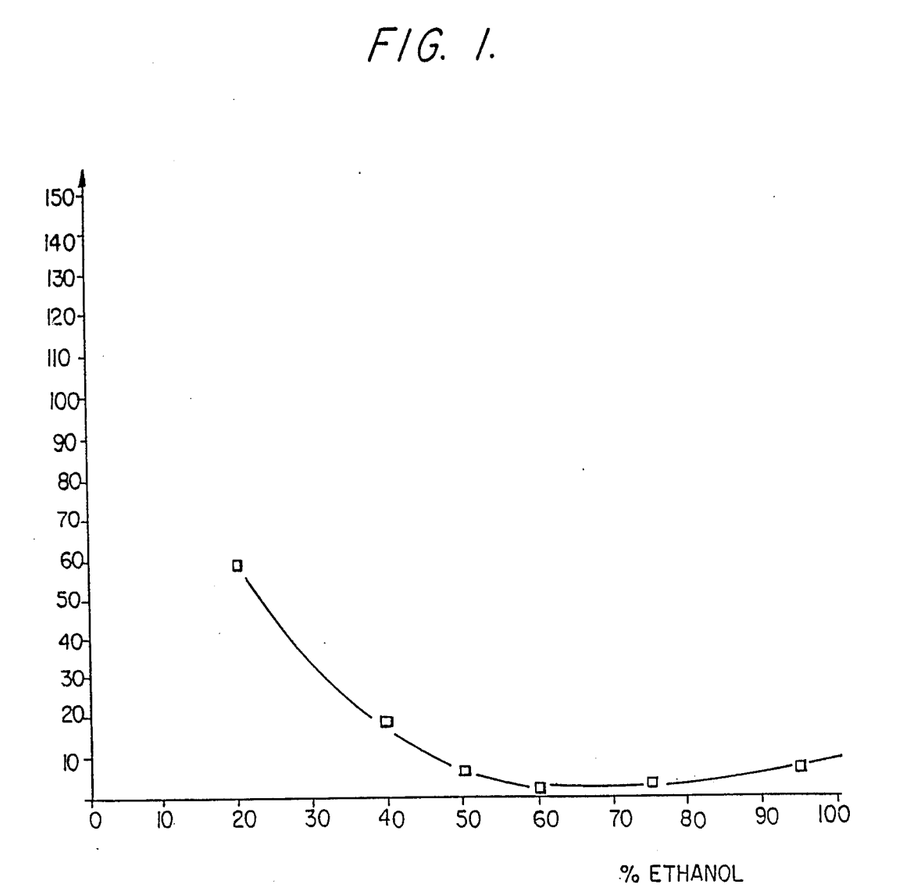

It has been shown that thiosulphate is indeed suitable for the preparation of a pure aqueous concentrated stock solution, but not the active substance I or a mixture thereof with thiosulphate:

FIG. 1 shows the solution volumes for 50 mg of I at room temperature (22° C.) in ethanol-water mixtures of various concentrations.

As is evident from FIG. 1, at least 40% ethanol is required for the preparation of a concentrated stock solution of I. On the other hand, sodium thiosulphate displayed only very limited solubility in over 40% ethanol, especially at temperatures <50° C. Mixtures of I and thiosulphate must not however, be heated in solution above 50° C., since otherwise the trimethaphan cation can decompose.

Therefore, the problem arose to find a physiologically acceptable solvent in which a mixture of I and thiosulphate in the weight ratio of about 1:1 to about 1:40 can dissolve to at least 5–10%, in a temperature range which for practical reasons should embrace temperatures between about 15° C. and about 35° C. Moreover, the concentrated solution should be able to dissolve without problem in the amount (250–1000 ml) of physiological sodium chloride solution or isotonic (5%) glucose solution required for final dilution.

Alternatively, a way was to be sought to enable the mixture of I and thiosulphate to be dissolved directly, rapidly and reliably in large volumes of the aforesaid infusion liquids with the avoidance of stock solutions.

It has now been found that 40–60% ethanol is suitable as a solvent for the preparation of concentrated stock solutions of mixtures of I and sodium thiosulphate up to a weight ratio 1:20 of the components.

For example, the mixture of 50 mg of I and 1000 mg of sodium thiosulphate pentahydrate dissolved at 37° C. in 10 ml
at 25° C. in 12 ml
at 20° C. in 13 ml and
at 15° C. in 15 ml of 55% ethanol.

Below the above-mentioned temperatures separation into two phases occurred immediately and thiosulphate crystallized out after a short time.

Figure 2:
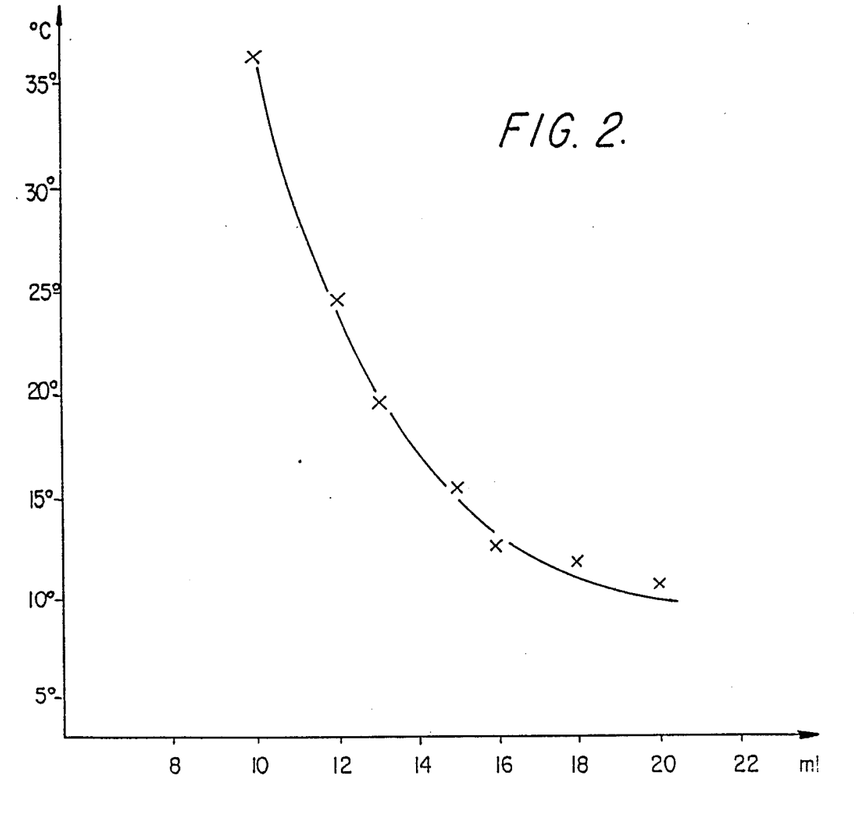

FIG. 2 shows the phase separation temperatures of a solution of 50 mg of I and 1000 mg of sodium thiosulphate pentahydrate in 55% ethanol as a function of the concentration.

In 50% ethanol the same mixture dissolved at 25° C. already in 8 ml. However, when it was cooled to temperature below 22°, phase separation occurred.

Thiosulphate has indeed a better solubility in weaker ethanol, but I is no longer completely soluble.

On the other hand, if the amount of thiosulphate in the mixture was reduced, then less or more concentrated ethanol (40–70%) could also be used for the preparation of a concentrated stock solution.

Figure 3:
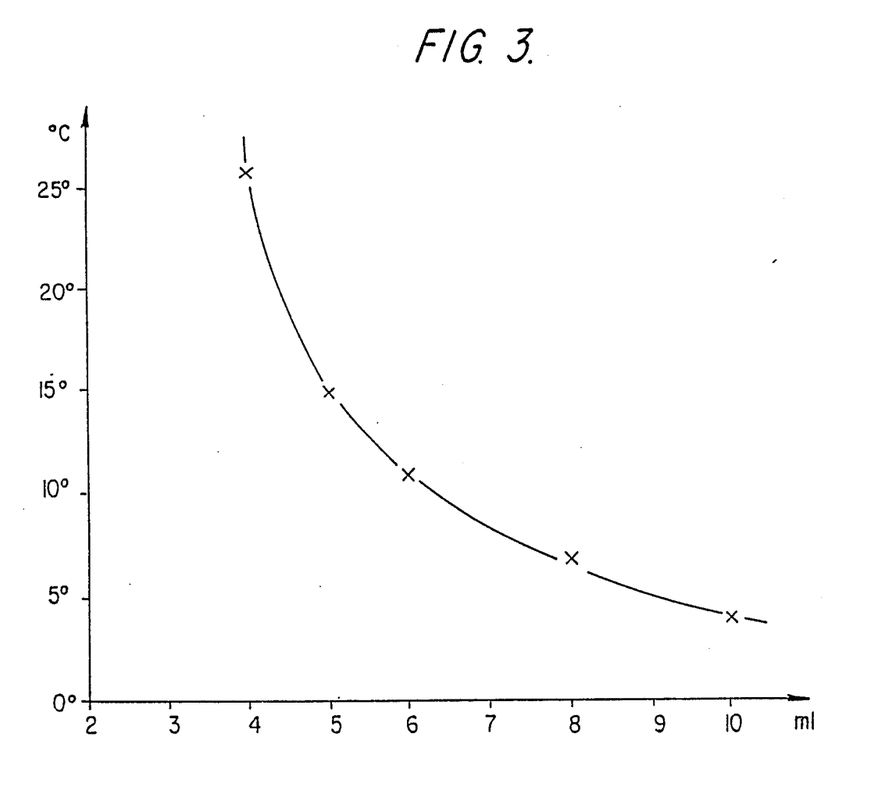

FIG. 3 shows the separation temperatures of a solution of 50 mg of I and 500 mg of sodium thiosulphate pentahydrate in 50% ethanol as a function of the concentration.

As FIG. 3 shows, a mixture in the weight ratio 1:10 (50+500 mg) already has a very good solubility in 50% ethanol: the latter mixture dissolved in accordance with FIG. 3 above 15° C. already in 5 ml of 50% ethanol.

The thus-obtained concentrated aqueous-alcoholic solutions dissolved without turbidity when poured into 220 ml of 0.9% sodium chloride solution or 5% glucose solution, thus their practical applicability is demonstrated.

Since the small amount of ethanol does not interfere with the infusion, but rather brings about an additional slight vasodilatory effect, this is an acceptable solution to the problem described above.

If the amount of thiosulphate is increased to above 1000 mg per 50 mg of I, then a concentrated stock solution in above 40% ethanol-water mixtures can no longer be prepared at 15° C.

However, it has surprisingly been found that in this case a direct solution of the mixture in the given amount of 0.9% sodium chloride solution or 5% glucose solution is possible when it is used in finest pulverized form, at best in micronized form. It has been found that a micronized mixture of 50 mg of I and 2000 mg of sodium thiosulphate pentahydrate dissolves within a few seconds in 250 ml of 5% glucose solution, while a coarsely ground mixture dissolved only after shaking for more than 10 minutes.

The methods in accordance with the invention described above thus enable not only the compound I, which is poorly soluble in water, but also mixtures of I and thiosulphate to be converted in a reliable manner into corresponding infusion solutions.

The mixtures or solutions described above can be stored without further additives with exclusion of light at room temperature and, if and when required, can be used for the preparation of infusion solutions. On the other hand, it is possible to add to the compositions small amounts of buffers (salts of weak acids, e.g. primary sodium phosphate, citrates, ascorbates or p-hydroxybenzoates), which at the same time can function as antioxidants and/or bacteriostats. The filling can also be effected under $N_2$. It is, however, known that nitroprussides themselves have weak bacteriostatic and, in higher concentrations, also bactericidal activity. The addition of the aforesaid agents is therefore not absolutely necessary.

The following Examples illustrate the present invention but are not intended to limit its extent. In these Examples all temperatures are given in degrees Centigrade.

EXAMPLE 1

29.8 g (0.1 mol) of sodium nitroprusside dihydrate are dissolved in 500 ml of water at room temperature. The reddish brown solution (solution A) obtained has to be protected from light.

119.4 g (0.2 mol) of (+)-trimethaphan camsylate are dissolved in 2000 ml of water and this solution is placed in a 3 l wide-necked vessel which is protected from light with aluminium foil. The solution A is added dropwise at room temperature with stirring and with occasional addition of seed crystals (or with occasional scratching). The velocity of the dropwise addition and the velocity of the stirring influence the size of the separating white to slightly yellowish crystals. The crystals are sucked off, rinsed several times with water and dried with the exclusion of light in vacuo at temperatures below 50°.

The compound thus obtained, (+)-bis-(trimethaphan)-nitroprusside, is only very slightly soluble in water, absolute ethanol and cyclohexane, but dissolves readily in aqueous ethanol.

If necessary, the compound can be recrystallized from aqueous ethanol or from methanol, optionally with addition of diethyl ether. On recrystallization from 70% ethanol there are obtained fine, yellowish-white needle clusters of melting point 200°–203° (decomposition). The compound is solvated depending on the solvent used. Elemental analysis (after drying, 18 h at room temperature/ $10^{-3}$ Torr over Siccapent):

$C_{49}H_{50}O_3N_{10}S_2Fe$ Molecular weight 947.0

Calculated C: 62.15 H: 5.32 N: 14.79 S: 6.77 $H_2O$ -  (%); Found 61.75; 5.48: 14.83; 6.89; 0.65 (%).

Systematic name: (+)-bis-/(3aS,8aR,8bR)-1,3-dibenzyl-decahydro-2-oxoimidazo[4,5-c]thieno[1,2-a]thiolium/-nitrosylpentacyanoferrate.

EXAMPLE 2

50 g of (+)-bis-(trimethaphan)-nitroprusside are dissolved at 25° in 2.8 l of 60% ethanol. The volume of the solution is brought to 3 l. After filtration over a Millipore filter, 3 ml portions of the solution are filled into sterile solvent ampoules manufactured from brown pyrogen-free glass.

The ampoules can even be stored at room temperature with exclusion of light. For the preparation of an infusion solution, the ampoule contents are dissolved in at least 220, at most 900 ml of sterile 0.09% sodium chloride solution or 5% glucose solution by vigorous shaking for a short time, whereafter the volume is brought to 250, 500 or 1000 ml. The infusion vessels and tubes are either to be covered with aluminium foil or must consist of material which is opaque to light.

The usual dosage amounts to 0.1–5 μg/kg.min, i.e. 0,5–100 μl/kg.min. depending on the concentration used.

EXAMPLE 3

50 mg of finely pulverized (+)-bis-(trimethaphan)-nitroprusside are filled into a sterilized, brown 5 ml flask closable with a synthetic stopper. 3 ml of 60% ethanol are sealed in a solvent ampoule and sterilized. Both substances can be stored for a very long time at room temperature and with exclusion of light. Immediately before use the solid substance is dissolved in the solvent and the thus-obtained stock solution is used for the preparation of the infusion solution.

EXAMPLE 4

A micronized mixture of 50 mg of (+)-bis-(trimethaphan)-nitroprusside and 2000 mg of sodium thiosulphate pentahydrate is filled into a brown dry ampoule or a brown vial supplied with a lid and stored at room temperature with exclusion of light.

Immediately before use the mixture is added with vigorous stirring or shaking to a measuring flask with at least 220 ml, at most 900 ml of 0.9% sodium chloride solution or 5% glucose solution, whereafter the volume is brought to 250, 500 or 1000 ml.

EXAMPLE 5

A finely pulverized mixture of 50 mg of (+)-bis-(trimethaphan)-nitroprusside and 250 mg of sodium thiosulphate pentahydrate is filled into a brown 5 ml solvent ampoule and 5 ml of 55% ethanol are added thereto. After closing, the ampoules are stored with the exclusion of light.

EXAMPLE 6

A micronized mixture of 25 g of (+)-bis-(trimethaphan)-nitroprusside and 125 g of sodium thiosulphate pentahydrate is dissolved in 2.5 l of 50% ethanol. The volume of the solution is brought to 3 l. After sterile filtration, 3 ml portions of the solution are filled into sterile, pyrogen-free brown solvent ampoules. The ampoules are sealed and stored with exclusion of light.

Immediately before use the contents of one ampoule are dissolved in at least 220 ml of 0.9% sodium chloride solution or 5% glucose solution and the volume is brought to 250, 500 or 1000 ml. The infusion solution is to be protected from the effect of light.

If the mid concentration were chosen (i.e. if the volume were brought to 500 ml), then the infusion dosage would amount in general to 2–100 μl/kg.min.

EXAMPLE 7

A brown solvent ampoule containing 50 mg of (+)-bis-(trimethaphan)-nitroprusside dissolved in 60% ethanol is packed together with a colourless solvent ampoule containing 250 mg of sodium thiosulphate dissolved in 3 ml of water. The ampoules are stored with exclusion of light.

Immediately before use the contents of the two ampoules are diluted with infusion liquid up to a volume of 250, 500 or 1000 ml. The obtained solution is to be protected from the effects of light.

EXAMPLE 8

25 mg of finely ground (+)-bis-(trimethaphan)-nitroprusside are mixed with 12.5 g of dry glucose. The mixture is ground again, if necessary, and then filled into a sterile PVC infusion bag or into a great dry ampoule. For preparing an infusion solution from the dry ampoule, the contents of the dry ampoule are dissolved in 220 ml of water, whereafter the volume is brought to 250 ml. For preparing an infusion solution in the infusion bag the contents of the infusion bag are dissolved by addition of 240 ml of water.

In both cases, the infusion solution contains (+)-bis-(trimethaphan)-nitroprusside in a concentration of 0.1 mg/ml (or 0.1 μg/μl) and 5% of glucose.

EXAMPLE 9

13.8 mg (52.8 μmoles) of anhydrous sodium nitroprusside, 42.3 mg (105.6 μmoles) of anhydrous (+)-trimethaphan chloride and 4.50 g of dry sodium chloride are mixed and finely ground with exclusion of light. The mixture is filled into a dry ampoule or into a PVC infusion bag. For preparing an infusion solution from the dry ampoule, the contents of the dry ampoule are added, immediately before the infusion, to 450 ml of water "pro injectionem" with vigourous stirring or shaking in order to prevent the poorly soluble (+)-bis-(trimethaphan)-nitroprusside which is formed in situ in finely divided form, from precipitating in the form of greater particles. Thereafter the volume is brought to 500 ml.

For preparing an infusion solution in the infusion bag, the appropriate amount of water (496 ml) is given into the bag and the contents of the bag are dissolved by shaking.

In both cases the infusion solution contains 0.9% of sodium chloride and (+)-bis-(trimethaphan)-nitroprusside in a concentration of 50 mg/liter (or 50 μg/ml or 0.05 μg/μl).

I claim:
1. Bis-(trimethaphan)-nitroprusside in isolated form.
2. The compound according to claim 1 which is (+)-bis-(trimethaphan)-nitroprusside.
3. A solvate of the compound according to claim 1 wherein the solvate is derived from a solvent which is a physiologically acceptable solvent.
4. A solvate according to claim 3 selected from the group consisting of hydrates and alcoholates.
5. A process for manufacturing the compound according to claim 1
and solvates thereof, said process comprising the steps of:
 (a) reacting an alkali nitroprusside with a soluble trimethaphan salt in a solution; and
 (b) isolating the bis-(trimethaphan)-nitroprusside product.
6. A process according to claim 5, wherein the reaction is carried out in a solvent containing the desired solvating agent.
7. The process according to claim 5 comprising performing step (a) in aqueous solution.
8. The process according to claim 5, wherein the solution of step (a) contains a solvent selected from the group consisting of one or more of water and alcohol.
9. The process according to claim 5, wherein the reactants of step (a) are sodium nitroprusside and trimethaphan camsylate.

10. A pharmaceutical composition containing, as an active substance, a pharmacologically effective amount of a material selected from the group consisting of the compound according to claim 1 and a solvate thereof.

11. A composition comprising a solution of the compound according to claim 2.

12. The composition according to claim 11 wherein the solvent is at least 40% ethanol.

13. A pharmaceutical composition containing a pharmaceutically acceptable excipient, and further containing, as an active substance, a pharamacologically effective amount of the compound according to claim 2.

14. An infusion solution comprising the pharmaceutical composition according to claim 13 and an appropriate amount of an infusion liquid.

15. A solvate of the compound according to claim 2 wherein the solvate is derived from a solvent which is a physiologically acceptable solvent.

16. A solvate according to claim 15 selected from the group consisting of hydrates and alcoholates.

17. The compound according to claim 16 which is (+)-bis-(trimethaphan)-nitroprusside semi-hydrate.

18. A pharmaceutical composition containing, as an active substance, a pharmacologically effective amount of the compound according to claim 17.

19. A pharmaceutical preparation comprising two separate containers, the first container containing an amount of at least 40% ethanol which is required to prepare a concentrated solution of the material in the second container when the first and second containers are admixed, and the second container containing a pharmacologically effective amount of the compound according to claim 17.

20. A method of lowering blood pressure in a mammal comprising the step of administering to said mammal, in an amount sufficient to lower the blood pressure of said mammal, an infusion solution containing the pharmaceutical composition according to claim 18.

21. The process according to claim 5 comprising performing step (a) with the alkali metal nitroprusside and the soluble trimethaphan salt in the molar ratio of approximately 1:2.

22. A pharmaceutical preparation comprising two containers, the first container containing an amount of at least 40% ethanol which is required to prepare a concentrated solution of the material in the second container when the first and second containers are admixed, and the second container containing a material selected from the group consisting of:
  (a) the active substance according to claim 10; and:
  (b) a mixture, in the weight ratio of 1:1 to 1:20, of said active substance and a material selected from the group consisting of sodium thiosulphate and its pentahydrate.

23. The pharmaceutical composition according to claim 10 containing a physiologically acceptable thiosulfate which is soluble in a solvent selected from the group consisting of water and aqueous ethanol.

24. The pharmaceutical composition according to claim 23 wherein the physiologically acceptable thiosulphate is selected from the group consisting of sodium thiosulphate and its pentahydrate.

25. The pharmaceutical composition according to claim 23 containing said active substance and the thiosulphate in a mixture in the form selected from the group consisting of a finely divided mixture and a micronized mixture.

* * * * *

UNITED STATES PATENT AND TRADEMARK OFFICE
CERTIFICATE OF CORRECTION

PATENT NO.   : 4,740,506                                   Page 1 of 3

DATED        : April 26, 1988

INVENTOR(S)  : Henning CIERPKA

It is certified that error appears in the above-identified patent and that said Letters Patent is hereby corrected as shown below:

At column 1, line 62, change "." to ---,--- after "(TMC)".

At column 4, line 49, insert ---%--- after "95".

At column 4, line 55, change "of" to ---or---.

At column 4, line 56, change "solution" to ---solutions---.

At column 5, line 26, change "43.6%)" to ---(43.6%)--- after "SNP".

At column 5, line 31, change "level to ---levels---.

At column 6, line 5, change "ot" to ---or---.

At column 6, line 47, change ":" to ---.---.

At column 7, line 23, change "temperature" to ---temperatures---.

At column 9, line 65, insert ---,--- after "use".

At column 10, line 11, insert ---,--- after "bag" and before "the".

At column 10, line 28, insert ---,--- after "-nitroprusside".

At column 10, line 30, insert ---,--- after "thereafter".

At column 10, line 34, insert ---,--- after "bag" and before "and".

At column 10, line 43, change "according to claim 1" to ---, according to claim 1,---.

At claim 10, line 45, change "according to claim 1" to ---, according to claim 1,---.

UNITED STATES PATENT AND TRADEMARK OFFICE
CERTIFICATE OF CORRECTION

PATENT NO. : 4,740,506

DATED : April 26, 1988

INVENTOR(S) : Henning CIERPKA

It is certified that error appears in the above-identified patent and that said Letters Patent is hereby corrected as shown below:

At column 10, line 48, change "according to claim 3" to ---, according to claim 3,---.
At column 10, line 50, change "according to claim 1" to ---, according to claim 1,---.
At column 10, line 58, insert ---,--- after "process".
At column 10, line 61, change "according to claim 5" to ---, according to claim 5,---.
At column 10, line 63, insert ---,--- after "process".
At column 10, line 66, insert ---,--- after "process".
At column 11, line 6, insert in claim 29 ---The compound, according to claim 2, which is in solid form.---.
At column 11, line 8, change "according to claim 11" to ---, according to claim 11,---.
At column 11, line 17, change "according to claim 2" to ---, according to claim 2,---.
At column 11, line 20, change "according to claim 15" to ---, according to claim 15---.

UNITED STATES PATENT AND TRADEMARK OFFICE
CERTIFICATE OF CORRECTION

PATENT NO. : 4,740,506
DATED : April 26, 1988
INVENTOR(S) : Henning CIERPKA It is certified that error appears in the above-identified patent and that said Letters Patent is hereby corrected as shown below:

At column 12, line 17 (line 8 of claim 22), delete ":" after "and".

Signed and Sealed this

Seventh Day of August, 1990

*Attest:*

HARRY F. MANBECK, JR.

*Attesting Officer*   *Commissioner of Patents and Trademarks*